(12) United States Patent
Darrow et al.

(10) Patent No.: US 7,179,887 B2
(45) Date of Patent: Feb. 20, 2007

(54) GUINEA PIG PROTEINASE-ACTIVATED RECEPTOR 4 AND ITS ACTIVATING PEPTIDE

(75) Inventors: Andrew L. Darrow, Lansdale, PA (US); Claudia K. Derian, Hatboro, PA (US); Michael F. Addo, Lansdale, PA (US); Patricia Andrade-Gordon, Doylestown, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/798,279

(22) Filed: Mar. 2, 2001

(65) Prior Publication Data

US 2006/0141451 A1    Jun. 29, 2006

(51) Int. Cl.
C07K 7/08 (2006.01)
C07K 14/705 (2006.01)
(52) U.S. Cl. .................... 530/350; 530/300; 530/380; 536/23.5
(58) Field of Classification Search .................... None
See application file for complete search history.

(56) References Cited

U.S. PATENT DOCUMENTS 6,111,075 A    8/2000    Xu et al.

FOREIGN PATENT DOCUMENTS

WO    WO 99/43809    9/1999
WO    WO 99/50415    10/1999
WO    WO02/070564 A2 *    9/2002

OTHER PUBLICATIONS

Nishikawa et al., Guinea pig platelets do not respond to GYPGKF, a protease-activated receptor-4-activating peptide: a property distinct from human platelets, Blood Coagulation and Fibrinolysis, 11:111-113, 2000.*
Andrade-Gordon et al., Administration of a potent antagonist of protease-activated receptor (PAR-1) attenuates vascular restenosis following balloon angioplasty in rats, J. Pharm. Exp. Therap. 298(1):34-42, 2001.*
Al-Ani, B., Saifeddine, M., and Hollenberg, M. D. (1995). Detection of functional receptors for the proteinase-activated-receptor-2 activating polypeptide, SLIGRL-NH2, in rat vascular and gastric smooth muscle. Can. J. Phys. Pharmacol. 73, 1203-1207.
Cheung, W.-m., Andrade-Gordon, P., Derian, C. K., and Damiano, B. P. (1998). Receptor-activating peptides distinguish thrombin receptor (PAR-1) and protease activated receptor 2 (PAR-2) mediated hemodynamic responses in vivo. Can. J. Physiol. Pharmacol. 76, 16-25.
Connolly, A. J., Ishihara, H., Kahn, M. L., Farese Jr., R. V., and Coughlin, S. R. (1996). Role of the thrombin receptor in development and evidence for a second receptor. Nature 381, 516-519.
Connolly, T. M., Condra, C., Feng, D.-M., Cook, J. J., Stranieri, M. T., Reilly, C. F., Nutt, R. F., and Gould, R. J. (1994). Species variability in platelet and other cellular responsiveness to thrombin receptor-derived peptides. Thromb. Haemostasis 72, 627-33.
Darrow, A. L., Fung-Leung, W.-P., Ye R. D., Santulli, R. J., Cheung, W.-M., Derian, C. K., Burns, C. L., Damiano, B. P., Zhou, L., Keenan, C. M., Peterson, P. A., and Andrade-Gordon, P. (1996). Biological consequences of thrombin receptor deficiency in mice. Thromb. Haemostasis 76, 860-866.
Derian, C. K., Santulli, R. J., Tomko, K. A., Haertlein, B. J., and Andrade-Gordon, P. (1995). Species differences in platelet responses to thrombin and SFLLRN. Receptor-mediated calcium mobilization and aggregation, and regulation by protein kinases. Thromb. Res. 78, 505-19.
Gersszten, R. E., Chen, J., Ishii, M., Ishii, K., Wang, L., Nanevicz, T., Turck, C. W., Vu, T.-K. H., and Coughlin, S. R. (1994). Specificity of the thrombin receptor for agonist peptide is defined by its extracellular surface. Nature (London) 368, 648-51.
Hollenberg, M. D., Saifeddine, M., and Al-Ani, B. (1996). Proteinase-activated receptor-2 in rat aorta: Structural requirements for agonist activity of receptor-activating peptides. Mol. Pharmacol 49, 229-233.
Ishihara, H., Connolly, A. J., Zeng, D., Kahn, M. L., Zheng, Y. W., Timmons, C., Tram, T., and Couglin, S. R. (1997). Protease-activated receptor 3 is a second thrombin receptor in humans. Nature (London) 386, 502-506.
Kahn, M., Ishii, K., Kuo, W.-L., Piper, M., Connolly, A., Shi, Y.-P., Wu, R., Lin, C. C., and Coughlin, S. R. (1996). Conserved structure and adjacent location of the thrombin receptor and protease-activated receptor 2 genes define a protease-activated receptor gene cluster. Mol. Med. (Cambridge, Mass.) 2, 349-357.
Kahn, M. L., Hammes, S. R., Botka, C., and Coughlin, S. R. (1998). Gene and locus structure and chromosomal localization of the protease-activated receptor gene family. J. Biol. Chem. 273, 23290-23296.
Kahn, M. L., Nakanishi-Matsui, M., Shapiro, M. J., Ishihara, H., and Coughlin, S. R. (1999). Protease-activated receptors 1 and 4 mediate activation of human platelets by thrombin. J. Clin. Invest. 103, 879-887.
Kahn, M. L., Zheng, Y.-W., Huang, W., Bigomia, V., Zeng, D., Moff, S., Farese, R. V., Jr., Tam, C., and Coughlin, S. R. (1998). A dual thrombin receptor system for platelet activation. Nature (London) 394, 690-694.
Kawabata, A., Kuroda, R., Minami, T., Kataoka, K., and Taneda, M. (1998). Increased vascular permeability by a specific agonist of protease-activated receptor-2 in rat hindpaw. Br. J. Pharmacol. 125, 419-422.
Li, F., Baykal, D., Horaist, C., Yan, C.-N., Carr, B. N., Rao, G. N., and Runge, M. S. (1996). Cloning and identification of regulatory sequences of the human thrombin receptor gene. J. Biol. Chem. 271, 26320-26328.

(Continued)

*Primary Examiner*—Lorraine Spector
*Assistant Examiner*—Claire M. Kaufman

(57) ABSTRACT

This invention relates to nucleic acid encoding guinea pig PAR 4 and to the protein encoded thereby. The guinea pig DNA and protein are useful for the development of models of human platelet aggregation. The invention further relates to an animal model to assess the role of PAR antagonists in thrombosis.

4 Claims, 4 Drawing Sheets

OTHER PUBLICATIONS

Nakanishi-Matsui, M., Zheng, Y.-W., Sulciner, D. J., Weiss, E. J., Ludeman, M. J., and Coughlin, S. R. (2000). PAR3 is a cofactor for PAR4 activation by thrombin. Nature (London) 404, 609-613.

Nishikawa, H., Kawabata, A., Kawai, K., and Kuroda, R. (2000). Guinea pig platelets do not respond to GYPGKF, a protease-activated receptor-4-activating peptide: a property distinct from human platelets. Blood Coagulation Fibrinolysis 11, 111-113.

Nystedt, S., Emilsson, K., Larsson, A.-K., Strombeck, B., and Sundelin, J. (1995). Molecular cloning and functional expression of the gene encoding the human proteinase-activated receptor 2. Eur. J. Biochem 232, 84-89.

Nystedt, S., Emilsson, K., Wahlestedt, C., and Sundelin, J. (1994). Molecular cloning of a potential proteinase activated receptor. *Proc. Natl. Acad. Sci. USA 91*, 9208-9212.

Nystedt, S., Larsson, A.-K., Aberg, H., and Sundelin, J. (1996). The mouse proteinase-activated receptor-2 cDNA and gene. Molecular cloning and functional expression. *J. Biol. Chem.* 270, 5950-5955.

Steinhoff, M., Vergnolle, N., Young, S. H., Tognetto, M., Arnadesi, S., Ennes, H. S., Trevisani, M., Hollenberg, M. D., Wallace, J. L., Caughey, G. H., Mitchell, S. E., Williams L. M., Geppetti, P., Mayer, E. A. and Bunnett, N. W. (2000). Agonists of proteinase-activated receptor 2 induce inflammation by a neurogenic mechanism. Nat. Med. (N.Y.) 6, 151-158.

Vu, T.-K. H., Hung, D. T., Wheaton, V. I., and Coughlin, S. R. (1991). Molecular cloning of a functional thrombin receptor reveals a novel proteolytic mechanism of receptor activation. *Cell 64*, 1057-1068.

Xu, W.-F., Andersen, H., Whitmore, T. E., Presnell, S. R., Yee, D. P., Ching, A., Gilbert, T., Davie, E. W., and Foster, D. C. (1998). Cloning and characterization of human protease-activated receptor 4. Proc. Natl. Acad. Sci. U. S. A. 95, 6642-6646.

Zheng, X.-L., Renaux, B., and Hollenberg, M. D. (1998). Parallel contractile signal transduction pathways activated by receptors for thrombin and epidermal growth factor-urogastrone in guinea pig gastric smooth muscle: blockade by inhibitors of mitogen-activated protein kinase-kinase and phosphatidyl inositol 3'-kinase. J. Pharmacol. Exp. Ther. 285, 325-334.

* cited by examiner

FIGURE 1

(SEQ.ID.NO.:1)

```
ATCCCACTTTATCTCTGCAGCTCCGGAAGCTGCCCTGGGTGACAAGGCAG
GAAGCGTTGGCCACTGACGAAGGGACGGCAGCATGTGGGAGCCCCTGCTG
                                   M   W   E   P   L   L
TGGCTGCTGGTGCTGGGGCTCGGCCTGGCAGGTAGCACCTCAACCCCCAG
 W   L   L   V   L   G   L   G   L   A   G   S   T   S   T   P   S
TGTCTATGATGAGGATGACGgtgagtggcctggccttgaggtggggactc
 V   Y   D   E   D   D
tgcccgggggagtagaatgtgggggccctggccccagtgctggcttctcc
cttccgagtcactgcctgtctggtgctagtcccaagctgggtccctgagc
cctctctccctctctgcagTGGGCTTGACAGGGCCTTGGGCCAGTTCTG
                    V   G   L   T   G   P   W   A   S   S   E
AGGCAGCAAGGACCCCACAGCAGGTGGCCCCACGCAGCTTCCCGGGCCAG
   A   A   R   T   P   Q   Q   V   A   P   R   S   F   P   G   Q
GCCTCTGCCAACGACAGTGATGTGCTGGAGCTGCCGGACCGCTTGCAGGT
   A   S   A   N   D   S   D   V   L   E   L   P   D   R   L   Q   V
GCTGCTACTGGGCTGGGCACCCACACGGCTGGTGCCCGCGCTATATGCGC
   L   L   L   G   W   A   P   T   R   L   V   P   A   L   Y   A   L
TGGCACTGGCCGTGGGGCTGCCGGCCAATGCACTGGCACTCTGGGTCCTG
   A   L   A   V   G   L   P   A   N   A   L   A   L   W   V   L
GCCCGACATGGTCCACGGCTGCCGGCCACCGCGCTGCTCATGAATCTGGC
   A   R   H   G   P   R   L   P   A   T   A   L   L   M   N   L   A
AGCCGCCGACCTACTGCTGGGCCTGGCACTGCCCCCACGCCTTGTCTACC
   A   A   D   L   L   L   G   L   A   L   P   P   R   L   V   Y   H
ACCTGCGTGGCCAGCGATGGCCCCTCGGGGAAGCGGCCTGCCGAGTATCC
   L   R   G   Q   R   W   P   L   G   E   A   A   C   R   V   S
ACAGCCACCCTCTACGGTCACATGTATGGTGCAGCGCTGTTGCTGGCTGC
   T   A   T   L   Y   G   H   M   Y   G   A   A   L   L   L   A   A
CATCAGCCTGGACCGCTACCTGGCGCTGGTGCACCCCCTGCGTGCCCGTG
```

FIGURE 1 con't

```
            I  S  L  D  R  Y  L  A  L  V  H  P  L  R  A  R  A
CGTTGCGGGGCCGCCGCCTGGCCACTGGGCTCTGCATGAGTGCCTGGCTA
     L  R  G  R  R  L  A  T  G  L  C  M  S  A  W  L
GGGGCCGCCACACTGGCCGCACCCCTGGCCCTGGGGCGCCAGACCTTCCG
  G  A  A  T  L  A  A  P  L  A  L  G  R  Q  T  F  R
CCTGGCAGGCTCCGGCCACCTGCTCTGTCATGATGTGCTGCCACTGGCCA
     L  A  G  S  G  H  L  L  C  H  D  V  L  P  L  A  T
CACAGACAGCCTTCTGGCGGCCAGCCTTTCTCTGTCTGGCTGCACTGGGC
        Q  T  A  F  W  R  P  A  F  L  C  L  A  A  L  G
TGCTTCCTGCCGCTGCTGCTCATGGCACTGTGCCATGGGGTCACACTGTG
     C  F  L  P  L  L  L  M  A  L  C  H  G  V  T  L  C
TGTGCTGGCAGCTGGTAGCCGGCGCCACAGCCATGCACTGCGACTCACGG
        V  L  A  A  G  S  R  R  H  S  H  A  L  R  L  T  A
CATTGGTGCTGGCTTCTGCTGTGGCCTTCTTTGTGCCCAGCAATGTGCTG
           L  V  L  A  S  A  V  A  F  F  V  P  S  N  V  L
CTGCTGTTGCACTACACAGACCCCAGCCCGGGTGCCGGTGGGGAACTGTA
     L  L  L  H  Y  T  D  P  S  P  G  A  G  G  E  L  Y
CGGTGCCTACCTGCCCAGCCTGGCGCTCAGCACCCTCAACAGCTGTGTTG
        G  A  Y  L  P  S  L  A  L  S  T  L  N  S  C  V  D
ACCCCTTCCTGTACTACTACGCATCCCCTGAGTTCCGGGACAAGGTGCGG
        P  F  L  Y  Y  Y  A  S  P  E  F  R  D  K  V  R
GCACAGCTGCGCTGCTGGTTGCCCAGGACCACTGCCACATCCCAGGGTTC
  A  Q  L  R  C  W  L  P  R  T  T  A  T  S  Q  G  S
CCAAGACGTGGGCAGTGCAGGCACCGGTACTCACTCCTTGCACCCCTGAT
  Q  D  V  G  S  A  G  T  G  T  H  S  L  H  P  *
GGCTCTGCGACCTTGGAGGTTGGAGGCCTCTGTCCTGAAGAGGGTACACA
```

GUINEA PIG PROTEINASE-ACTIVATED RECEPTOR 4 AND ITS ACTIVATING PEPTIDE

BACKGROUND OF THE INVENTION

Proteinase-activated receptors (PARs) are part of a distinct and growing class of G-protein-coupled receptors (GPCRs) with the first PAR, the thrombin receptor, now termed PAR-1, first identified ten years ago (Vu et al. (1991). *Cell* 64:1057–1068). PAR-1 becomes activated following proteolytic cleavage by the serine proteinase thrombin within the amino-terminus. Substantial evidence indicates that the neo-amino terminus, generated after proteolytic cleavage site is the PAR-1's own tethered ligand. Binding of the tethered ligand to the receptor domain leads to receptor activation. Thus, the PAR class of GPCRs are unique in that part of the polypeptide sequence of the receptor encodes the sequence of the receptor's ligand or activating protein (AP).

Additional PARs have been identified. These include PAR-2 (Nystedt et al. (1994). *Proc. Natl. Acad. Sci. USA* 9208–9212) and PAR-3 (Ishihara et al. (1997). *Nature (London)* 386:502–506). Most recently the human (Xu et al. (1998). *Proc. Natl. Acad. Sci. U.S.A.* 95:6642–6646) and murine cDNAs (Kahn et al. (1998). *Nature (London)* 394: 690–694) for PAR-4 have been identified.

Human platelets aggregate in response to thrombin and this response is mediated through PAR-1. A reduction in PAR-1 results in a decrease in thrombin-induced platelet aggregation. The aggregation of human platelets can be reproduced by the exogenous addition of both human PAR-1 AP (SFLLRN-NH2, SEQ ID No.: 8) and murine PAR-1 AP (sequence identical to human PAR-1 AP), however, rodent platelets respond differently to thrombin. A deficiency in mouse PAR-1 does not reduce thrombin-induced platelet aggregation in the mouse (Connolly et al. (1996). *Nature* 381:516–519; Darrow et al. (1996). *Thromb. Haemostasis* 76:860–866) demonstrating that the aggregation of murine platelets is mediated through a different receptor for thrombin. Moreover, human AP won't activate mouse PAR-4 indicating that the mouse model may not be an accurate model for understanding human PAR-4 activation. The primary thrombin receptor in the mouse is now known to be PAR-4 (Kahn et al. (1998) *Nature (London)* 394:690–694) and this is likely to be the rat receptor as well. Recent evidence indicates that human platelets respond to thrombin through a combination of PAR1 and PAR4 (Kahn et al. (1999). *J. Clin. Invest.* 103:879–887).

Therefore a need exists to develop a small animal model that more reproducibly mimics human thrombosis and platelet function.

SUMMARY OF THE INVENTION

The present invention provides nucleic acids encoding guinea pig PAR4, expression vectors containing guinea pig PAR4, and cells expressing recombinant guinea pig PAR4 protein. The guinea pig PAR4 protein is useful as a small animal model of thrombosis. The present invention also provides guinea pig PAR4 activating peptides. These peptides are useful in small animal models of human thrombosis, and are useful as ligands to activate human PAR4.

In one aspect, this invention relates to an isolated and purified nucleic acid molecule encoding guinea pig PAR-4 protein, said molecule selected from the group consisting of: (a) a nucleic acid molecule encoding a protein having at least a 75% identity to a polypeptide comprising amino acids 1 to 388 of SEQ ID NO:3; (b) a nucleic acid molecule which is complementary to the polynucleotide of (a); (c) a nucleic acid molecule comprising at least 15 sequential bases of the polynucleotide of (a) or (b); and (d) a nucleic acid molecule that hybridizes under stringent conditions to the polynucleotide molecule of (a). In one embodiment the nucleic acid molecule is RNA or DNA and preferably has the nucleic acid sequence of SEQ.ID.NO.:1 or SEQ.ID.NO.:2. In another embodiment the nucleic acid encodes a PAR-4 fusion protein comprising at least amino acids 219 to 243 of guinea pig PAR4.

The invention further relates to vectors for the expression of a guinea pig PAR-4 protein in a recombinant host, wherein the vector comprises nucleic acid molecule that hybridizes under stringent conditions to the polynucleotide molecule of SEQ ID NO:2. In one embodiment the expression vector comprises nucleic acid corresponding to the nucleotide sequence of SEQ.ID.NO.:1 or SEQ.ID.NO.:2 and preferably encodes the guinea pig PAR-4 protein of SEQ ID NO:3. In another embodiment the expression vector comprises genomic DNA encoding guinea pig PAR-4 protein.

The invention also relates to recombinant host cells that include expression vectors comprising a nucleic acid molecule that hybridizes under stringent conditions to the polynucleotide molecule of SEQ ID NO:2. In one embodiment the expression vector comprises the nucleic acid molecule has the nucleotide sequence of SEQ.ID.NO.:1 or SEQ.ID.NO.:2.

The invention further relates to a substantially pure protein comprising a sequence of least 15 consecutive amino acids corresponding to amino acids 219 through 243 of SEQ ID NO:3. In one embodiment the protein has a molecular weight of between 41–55 kD. In another embodiment the protein has the amino acid sequence as described in SEQ.ID.NO.:3. The invention also relates to a peptide consisting of at least 15 consecutive amino acids from SEQ ID NO:3.

The invention also relates to antibody immunologically reactive with guinea pig PAR-4 protein. Preferably the antibody is monospecific, that is it specifically reacts with guinea pig PAR-4 protein but not with human or mouse PAR-4 protein. In one embodiment the antibody is monoclonal. In another, the antibody of claim 16, wherein the antibody blocks activity of the guinea pig PAR-4 protein.

The invention also includes cellular membrane fractions obtained from cells that contain guinea pig PAR-4 protein. In one embodiment, the fraction comprises a protein having a sequence of least 15 consecutive amino acids corresponding to amino acids 219 through 243 of SEQ ID NO:3.

The invention further relates to methods for expressing guinea pig PAR-4 protein in a recombinant host cell, comprising the steps of: introducing an expression vector capable of expressing guinea pig PAR-4 into suitable host cells; and culturing the host cells under conditions which allow expression of the guinea pig PAR-4 protein.

The invention also relates to a Protease Activated Receptor (PAR) activating peptide comprising the sequence SFPGQ(X)$_n$, where X is any amino acid or amino acid derivative and wherein n is 0–30 and to monospecific antibody immunologically reactive with the activating peptide.

In another method, the method comprises the steps of: (a) admixing in an aqueous environment a guinea pig PAR-4 activating peptide (AP) with a cell; (b) incubating the PAR-4 activating peptide and the cell for a predetermined amount of time; and (c) measuring the interaction of the peptide with the cells. In one embodiment, the method occurs in vitro. In another, the method occurs in vivo. In another the interaction of the peptide with the cell is detected by measuring the activation of a Protease Activated Receptor (PAR).

The invention further relates to a method for promoting human platelet aggregation comprising the step of combining an aggregating amount of an activating peptide with human platelets wherein the activating peptide comprises the sequence SFPGQ(X)$_n$ where x is any amino acid and n is a number between 0 and 30.

The invention further relates to methods for determining whether a substance is capable of inhibiting guinea pig PAR-4 activity in a guinea pig comprising the steps of: giving a test substance and an activating peptide to a guinea pig, wherein the activating peptide comprises the sequence SFPGQ(X)$_n$ where x is any amino acid and n is a number between 0 and 30; and measuring the ability of the test substance to inhibit PAR-4 activation in the guinea pig as compared to a control guinea pig that did not receive the test substance.

In another embodiment, a method for determining whether a substance capable of interfering with the interaction between an activating peptide and a PAR-4 protein is disclosed, the method comprises the steps of: adding a test substance and an activating peptide to a cell membrane composition comprising a PAR-4 protein wherein the activating peptide comprises the sequence SFPGQ(X)$_n$ where x is any amino acid and n is a number between 0 and 30; measuring the amount of binding of the activating peptide to the cell membrane composition; and comparing the amount of binding of the activating peptide to the cell membrane composition with the amount of binding of the activating peptide in control cells receiving no test substance. In one aspect the cell membrane composition is a cell membrane fraction. In another, the cell membrane composition is part of an intact cell, an isolated tissue or organ sample. In this method, the cells can be platelets and the measuring the amount of binding step comprises measuring the amount of platelet aggregation, calcium mobilization, ADP degranulation or cell shape change. In one aspect the method is performed in a guinea pig. In another aspect the activating peptide is labeled and the measuring the amount of binding step comprises measuring the amount of label bound to the cell membrane composition.

BRIEF DESCRIPTION OF THE DRAWING

FIG. 1 is a map of nucleotides 301 to 1750 of the guinea pig PAR-4 gene (SEQ.ID.NO.:1) with translated amino acids encoded by exons 1 and 2 and the intervening sequence in lower case is shown.

DETAILED DESCRIPTION OF THE INVENTION

Definitions

Figure 2:
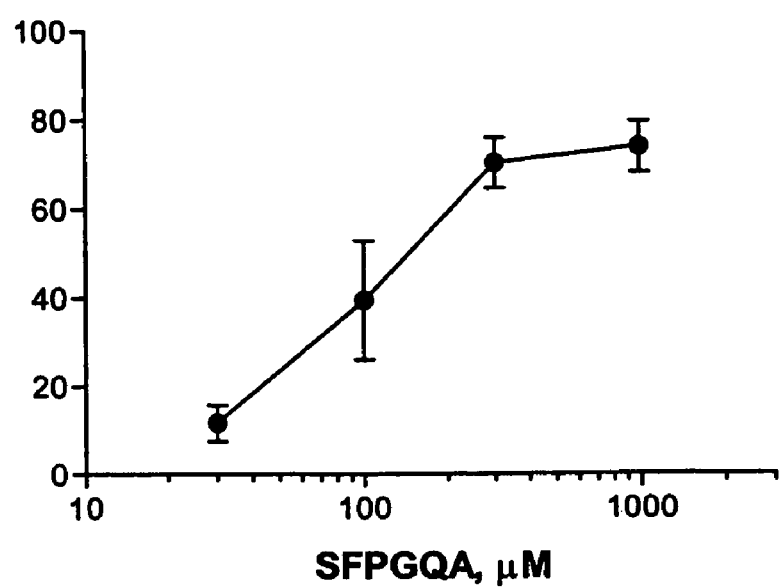
FIG. 2 is a graph illustrating the induction of guinea pig platelet aggregation by guinea pig PAR-4 AP.

The term "protein domain" as used herein refers to a region of a protein that may have a particular three-dimensional structure that can independent from the remainder of the protein. This region may maintain a particular activity associated with the domain's function within the protein. These activities include, for example, enzymatic activity, creation of a recognition motif for another molecule, or act to provide the necessary structural components for a protein to exist in a particular environment. Protein domains are usually evolutionarily conserved regions of proteins, both within a protein family and within protein superfamilies that perform similar functions. The term "protein superfamily" as used herein includes proteins whose evolutionary relationship may not be entirely established or may be distant by accepted phylogenetic standards, but show similar three dimensional structure or proteins that display one or more unique consensus of critical amino acids. The term "protein family", as used herein, refers to proteins whose evolutionary relationship has been established by accepted phylogenic standards.

The term "fusion protein" as used herein refers to protein constructs that are the result of combining more than one protein domain or linker region for the purpose of gaining the combined functions of the combined domain or linker region. Fusion proteins can be created by molecular cloning of the nucleotide sequences encoding such domains to produce a new polynucleotide sequence that encodes the desired fusion protein. Alternatively, creation of a fusion protein may be accomplished by chemically joining two proteins, as is known in the art.

The term "linker region" or "linker domain" or similar such descriptive terms as used herein refers to a polynucleotide or polypeptide sequence used in the construction of a cloning vector or fusion protein. Linker regions can be used, for example, to introduce one or more restriction cloning sites into a nucleotide sequence, introduce a flexible component or space-creating region between two protein domains, create an affinity tag for specific molecule interaction, and the like. Linker regions may be introduced into a fusion protein using any number of methods known to those in the art of polypeptide chemistry or molecular biology.

The term "cloning site" or "polycloning site" as used herein refers to a region of a nucleotide sequence that has one or more available restriction endonuclease cleavage recognition sequences. These nucleotide sequences may be used for a variety of purposes including, but not limited to, their introduction into DNA vectors to create novel fusion proteins or to introduce specific site-directed mutations. It is well known by those of ordinary skill in the art that cloning sites can be engineered into a desired location by silent mutation, conserved mutation, or introduction of a linker region that contains the desired restriction endonuclease recognition sequence.

The term "tag" as used herein refers to an amino acid sequence or a nucleotide sequence encoding an amino acid sequence that facilitates isolation, purification or detection of a protein containing the tag. A wide variety of tags are known to those skilled in the art and are suitable for use in the present invention. Suitable tags include, but are not limited to, HA peptide, polyhistidine peptides, biotin/avidin, and other antibody epitope binding sites.

The present invention began with the examination of aggregation responses of platelets from the guinea pig (*Cavia porcellus*). To characterize the diversity of thrombin receptors on guinea pig platelets, the stimulation of platelet aggregation using specific activating peptides was evaluated. Activating peptides corresponding to human PAR-1 (SFLLRN-NH2, SEQ ID No.:8), human PAR-4 (GYPGQV-NH2, SEQ ID No.:9), and murine PAR-4 (GYPGKF-NH2, SEQ ID No.:10) were tested on isolated guinea pig platelets. Human PAR-1 and PAR-4 APs induced human platelet aggregation. Surprisingly, we found that only the PAR-1 AP induced guinea pig platelet aggregation, whereas the PAR-4

APs did not. Similarly, it is known that guinea pig platelets do not respond to murine PAR-4 AP (Nishikawa et al. (2000). *Blood Coagulation Fibrinolysis* 11:111–113).

Isolation of Guinea Pig PAR-4 Nucleic Acid

To follow up on the finding that guinea pig platelets are unresponsive to known PAR-4 APs, the guinea pig PAR-4 gene and corresponding cDNA was cloned to determine the sequence the PAR-4 AP in this species. DNA encoding guinea pig PAR-4 gene that was isolated from a guinea pig genomic library. Subsequently, the structure of the corresponding guinea pig PAR-4 cDNA was determined from its partial isolation from guinea pig platelets. The result is SEQ ID No.:1 and SEQ ID No.:2 respectively. The guinea pig PAR-4 gene is comprised of two exons separated by a 150-bp intron with the first exon encoding predominantly the signal sequence. The second exon contains the AP sequence and the remainder of the coding sequence. The guinea pig PAR-4 cDNA encodes a polypeptide of about 388 amino acids with 71.2% identity in a 386 nucleotide (nt) overlap with human PAR-4 (Genbank Accession AF055917) and 66.6% identity in a 392 nt overlap with murine PAR-4 (Genbank Accession AF080215). Significantly, sequence analysis revealed that guinea pig PAR-4 contains the activation motif SFPGQA (SEQ ID No.:7), which diverges from the motifs in human (GYPGQV, SEQ ID No.: 9) or murine (GYPGKF, SEQ ID No.: 10) PAR-4.

The nucleic acid sequence of SEQ ID No.1 is provided below:

```
GGTGCCCGGGTTCTGGGGCCCTGGAAAGGCTGGAGACAGCA
CAGTCACTTTCCGGCCATCTCTGTGTGGGACTGGAGCAGGAA
ACGGGCCACTTGGGAGCCCCACCCTCAGTTTCTGTTACTGTC
AGGGGCCCGGCCTGGCCACTGCCTGGAAAATCCCTGTGGTCA
CCCTGGGACCACTCCACGGACCACTCTGCTCTGCTGGCCTGT
GGAGGACACCATAGAGACAGCGGGAACAGGCCACCTGCCCA
CTCACACACTCGCAGCCTCCCTGGTGGCCTTGGGAGTACCAG
GTCACCACATCCCACTTTATCTCTGCAGCTCCGGAAGCTGCC
CTGGGTGACAAGGCAGGAAGCGTTGGCCACTGACGAAGGGA
CGGCAGCATGTGGGAGCCCCTGCTGTGGCTGCTGGTGCTGGG
GCTCGGCCTGGCAGGTAGCACCTCAACCCCCAGTGTCTATGA
TGAGGATGACGGTGAGTGGCCTGGCCTTGAGGTGGGGACTCT
GCCCGGGGGAGTAGAATGTGGGGGCCCTGGCCCCAGTGCTG
GCTTCTCCCTTCCGAGTCACTGCCTGTCTGGTGCTAGTCCCAA
GCTGGGTCCCTGAGCCCTCTCTCCCCTCTCTGCAGTGGGCTTG
ACAGGGCCTTGGGCCAGTTCTGAGGCAGCAAGGACCCCACA
GCAGGTGGCCCCACGCAGCTTCCCGGGCCAGGCCTCTGCCAA
CGACAGTGATGTGCTGGAGCTGCCGGACCGCTTGCAGGTGCT
GCTACTGGGCTGGGCACCCACACGGCTGGTGCCCGCGCTATA
TGCGCTGGCACTGGCCGTGGGGCTGCCGGCCAATGCACTGGC
ACTCTGGGTCCTGGCCCGACATGGTCCACGGCTGCCGGCCAC
CGCGCTGCTCATGAATCTGGCAGCCGCCGACCTACTGCTGGG
CCTGGCACTGCCCCCACGCCTTGTCTACCACCTGCGTGGCCA
GCGATGGCCCCTCGGGGAAGCGGCCTGCCGAGTATCCACAG
CCACCCTCTACGGTCACATGTATGGTGCAGCGCTGTTGCTGG
CTGCCATCAGCCTGGACCGCTACCTGGCGCTGGTGCACCCCC
TGCGTGCCCGTGCGTTGCGGGGCCGCCGCCTGGCCACTGGGC
TCTGCATGAGTGCCTGGCTAGGGGCCGCCACACTGGCCGCAC
CCCTGGCCCTGGGGCGCCAGACCTTCCGCCTGGCAGGCTCCG
GCCACCTGCTCTGTCATGATGTGCTGCCACTGGCCACACAGA
CAGCCTTCTGGCGGCCAGCCTTTCTCTGTCTGGCTGCACTGG
GCTGCTTCCTGCCGCTGCTGCTCATGGCACTGTGCCATGGGG
TCACACTGTGTGTGCTGGCAGCTGGTAGCCGGCGCCACAGCC
ATGCACTGCGACTCACGGCATTGGTGCTGGCTTCTGCTGTGG
CCTTCTTTGTGCCCAGCAATGTGCTGCTGCTGTTGCACTACAC
AGACCCCAGCCCGGGTGCCGGTGGGGAACTGTACGGTGCCT
ACCTGCCCAGCCTGGCGCTCAGCACCCTCAACAGCTGTGTTG
ACCCCTTCCTGTACTACTACGCATCCCCTGAGTTCCGGGACA
AGGTGCGGGCACAGCTGCGCTGCTGGTTGCCCAGGACCACT
GCCACATCCCAGGGTTCCCAAGACGTGGGCAGTGCAGGCAC
CGGTACTCACTCCTTGCACCCCTGATGGCTCTGCGACCTTGG
AGGTTGGAGGCCTCTGTCCTGAAGAGGGTACACAGTGGCCCT
GGCCCAACGCAGCTGGAAGTGCTCTCCACCCAGAAGTCCCTG
CCACTGTGGACCCCATGGGTCACGGTCACAGCAGCCCTGGG
AACCCAAGGGCTCAGGTGCAGGTCCCCACGATGTGGCCCCA
CTGCAGCCCAGCCTGTGCAGCCCTGCCTCCCTGGAAGCCGGC
CTGCTTTCCTCTCCACCCCGCCCTGCCCCCCACACCCACCACC
TGGTCCCTGTCCCATCTGCCTGGCCTCATAGGGTGGGGTGG
GGACACTTGAGTTGGGCTCACTGTGGTCCATGATGCTTCCAA
TAAAACCTTAAAGGACATGAGACAGCAAAATGTCTGGCCCT
GCACAAACAGGGACAGTACACCCTGGCACTAAGGTGGGTCT
GGGGAGGGCAGGAGCCTCAGTGATGGGAGGGCCCTGTGGGG
AGAGGGGCAGAGGCAGGCCAAGGGATGGCCAGGGTGCTGG
ATGGGTCGCCAGGCAGCTGGGTACAGCAGTCCAAGGGTACA
GGAAAGTGGCCTGCAGCATTTGACAGCACTAGGGGAGGCCA
CTCTGGGGCCTGACCCAGGGCTCCTGTGCCAGCCGAGCTTCT
GCCCACCAGGCTGCACCAGGCCCACTATGCTGATATAGGG
GCTTGCTAACTTGCCCAGGCTGGTCCTGAACTTGCTACCTTCT
TCATCT
```

Neither the amino acid sequence nor the nucleotide sequence of guinea pig PAR-4 was previously known. These sequences are provided here or alternatively can be identified de novo from a wide variety of guinea pig cells and cell types. Cells capable of natively expressing guinea pig PAR-4 include, but are not limited to, guinea pig platelets or other tissues or cells from this species that correspond to cells or tissues that are known to express the orthologous human or murine PAR-4 mRNA (Xu et al. (1998). *Proc. Natl. Acad. Sci. U.S.A.* 95:6642–6646; Kahn et al. (1998). *Nature* (*London*) 394:690–694).

Other cells capable of GP PAR-4 expression may be identified by screening for guinea pig PAR-4 activity in cell extracts or in whole cell assays, as described herein. Cells that possess guinea pig PAR-4 activity in any one of these assays can be used in the isolation of guinea pig PAR-4 DNA or mRNA. Preferably, guinea pig PAR-4 AP is used as a selective activator of guinea pig PAR-4 and can be used in the assays of this invention to identify cells expressing guinea pig PAR-4 activity. The protease thrombin is known to activate both PAR-1 and PAR-4 and is therefore not selective between these two receptor subtypes. This is of significance in surveys of PAR-4 activity not only within various guinea pig tissue types but also when using cells from potentially related mammalian species encoding orthologs of this novel form of PAR-4 AP.

Any of a variety of procedures known in the art may be used to molecularly clone guinea pig PAR-4 DNA from guinea pig cells expressing the PAR-4 protein. These methods include, but are not limited to, direct functional expression of the guinea pig PAR-4 genes following the construction of a guinea pig PAR-4-containing cDNA library in an appropriate expression vector system. Another method is to screen a guinea pig PAR-4-containing cDNA library constructed in a bacteriophage or plasmid shuttle vector using a labeled oligonucleotide probe designed from the amino acid sequence encoded by the guinea pig PAR-4 gene or cDNA. Alternatively a guinea pig PAR-4-containing cDNA library constructed in a bacteriophage or plasmid shuttle vector can be screened with a partial cDNA encoding the guinea pig PAR-4 protein. This partial cDNA is obtained by the specific PCR amplification of guinea pig PAR-4 DNA fragments through the design of degenerate oligonucleotide primers from the amino acid sequence of the purified guinea pig PAR-4 protein.

Guinea pig PAR-4 cDNA can also be obtained by isolating RNA from guinea pig PAR-4-producing cells and translating the RNA into protein via an in vitro or an in vivo translation system. The translation of the RNA into a peptide, polypeptide or a protein will result in the production of at least a portion of the guinea pig PAR-4 protein which can be identified by, for example, immunological reactivity with an anti-guinea pig PAR-4 antibody or by biological activity of guinea pig PAR-4 protein. In this method, pools of RNA isolated from guinea pig PAR-4-producing cells can be analyzed for the presence of an RNA that encodes at least a portion of the guinea pig PAR-4 protein. Further fractionation of the RNA pool can be done to purify the guinea pig PAR-4 RNA from non-guinea pig PAR-4 RNA. The peptide or protein produced by this method may be analyzed to provide amino acid sequences, which in turn are used to provide primers for production of guinea pig PAR-4 cDNA. Alternatively, the RNA used for translation can be analyzed to provide nucleotide sequences encoding guinea pig PAR-4 and produce probes for the production of guinea pig PAR-4 cDNA. These methods are known in the art and can be found in, for example, Maniatis, T., Fritsch, E. F., Sambrook, J. in *Molecular Cloning: A Laboratory Manual*, Second Edition, Cold Spring Harbor Laboratory Press, Cold Spring Harbor, N.Y. 1989.

It is readily apparent to those skilled in the art that other types of libraries, as well as libraries constructed from other guinea pig cells or other cell types, may be useful for isolating guinea pig PAR-4-encoding DNA. Other types of libraries include, but are not limited to, cDNA libraries derived from other cells, and genomic DNA libraries that include YAC (yeast artificial chromosome) and cosmid libraries from organisms other than guinea pig that expresses a PAR-4 subtype responding to thrombin but are nonresponsive to both human or murine PAR-4 AP. Advantageously, these libraries use vector systems that incorporate genomic DNA into the vector.

It is also readily apparent to those skilled in the art that suitable cDNA libraries may be prepared from cells or cell lines which have guinea pig PAR-4 activity. The selection of cells or cell lines for use in preparing a cDNA library to isolate guinea pig PAR-4 cDNA may be done by first measuring cell associated guinea pig PAR-4 activity through the detection of guinea pig PAR-4-associated biological activity. Examples of guinea pig PAR-4 associated biological activity that can be used to measure guinea pig PAR-4 activity include calcium mobilization or inositol phosphate turnover as a signal transduction readout. In these cases the assay is facilitated by the use of the guinea pig PAR-4 AP as described here because both human and murine PAR-4 APs lack a detectable response on the guinea pig PAR-4 subtype.

Preparation of cDNA libraries can be performed by standard techniques well known in the art. Well known cDNA library construction techniques can be found for example, in Maniatis, T., et al., supra.

It is also readily apparent to those skilled in the art that DNA encoding guinea pig PAR-4 may also be isolated from a suitable genomic DNA library. Construction of genomic DNA libraries can be performed by standard techniques well known in the art. Well known genomic DNA library construction techniques can be found in Maniatis, T., et al., supra.

In order to clone the guinea pig PAR-4 gene by the above methods, the amino acid sequence of guinea pig PAR-4 may be necessary. The sequence is provided here; however, protein can also be isolated de novo. Guinea pig PAR-4 protein can be purified and a partial amino acid sequence determined by automated sequenators. It is not necessary to determine the entire amino acid sequence, but the linear sequence of two regions of 6 to 8 amino acids from the protein is determined for the production of primers for PCR amplification of a partial guinea pig PAR-4 DNA fragment. Similarly, PCR primers, including degenerate primers, can be created using SEQ ID NO:1 or SEQ ID NO:2.

The nucleotide sequence of the guinea pig PAR-4 cDNA (SEQ.ID.NO.:2) is provided below:

```
TCCGGAAGCTGCCCTGGGTGACAAGGCAGGAAGCGTTGGCCA

CTGACGAAGGGACGGCAGCATGTGGGAGCCCCTGCTGTGGCT

GCTGGTGCTGGGGCTCGGCCTGGCAGGTAGCACCTCAACCCCC

AGTGTCTATGATGAGGATGACGTGGGCTTGACAGGGCCTTGG

GCCAGTTCTGAGGCAGCAAGGACCCCACAGCAGGTGGCCCCA

CGCAGCTTCCCGGGCCAGGCCTCTGCCAACGACAGTGATGTGC

TGGAGCTGCCGGACCGCTTGCAGGTGCTGCTACTGGGCTGGGC

ACCCACACGGCTGGTGCCCGCGCTATATGCGCTGGCACTGGCC

GTGGGGCTGCCGGCCAATGCACTGGCACTCTGGGTCCTGGCCC

GACATGGTCCACGGCTGCCGGCCACCGCGCTGCTCATGAATCT
```

```
                            -continued
GGCAGCCGCCGACCTACTGCTGGGCCTGGCACTGCCCCACG

CCTTGTCTACCACCTGCGTGGCCAGCGATGGCCCCTCGGGGAA

GCGGCCTGCCGAGTATCCACAGCCACCCTCTACGGTCACATGT

ATGGTGCAGCGCTGTTGCTGGCTGCCATCAGCCTGGACCGCTA

CCTGGCGCTGGTGCACCCCCTGCGTGCCCGTGCGTTGCGGGGC

CGCCGCCTGGCCACTGGGCTCTGCATGAGTGCCTGGCTAGGGG

CCGCCACACTGGCCGCACCCCTGGCCCTGGGGCGCCAGACCTT

CCGCCTGGCAGGCTCCGGCCACCTGCTCTGTCATGATGTGCTG

CCACTGGCCACACAGACAGCCTTCTGGCGGCCAGCCTTTCTCT

GTCTGGCTGCACTGGGCTGCTTCCTGCCGCTGCTGCTCATGGC

ACTGTGCCATGGGGTCACACTGTGTGTGCTGGCAGCTGGTAGC

CGGCGCCACAGCCATGCACTGCGACTCACGGCATTGGTGCTG

GCTTCTGCTGTGGCCTTCTTTGTGCCCAGCAATGTGCTGCTGCT

GTTGCACTACACAGACCCCAGCCCGGGTGCCGGTGGGGAACT

GTACGGTGCCTACCTGCCCAGCCTGGCGCTCAGCACCCTCAAC

AGCTGTGTTGACCCCTTCCTGTACTACTACGCATCCCCTGAGTT

CCGGGACAAGGTGCGGGCACAGCTGCGCTGCTGGTTGCCCAG

GACCACTGCCACATCCCAGGGTTCCCAAGACGTGGGCAGTGC

AGGCACCGGTACTCACTCCTTGCACCCCTGA
```

Once suitable amino acid sequences have been identified, the DNA primers corresponding to nucleic acid encoding the amino acid sequences are synthesized. Because the genetic code is degenerate, more than one codon may be used to encode a particular amino acid, and therefore, the amino acid sequence can be encoded by any of a set of similar DNA oligonucleotides. Only one member of the set will be identical to the guinea pig PAR-4 sequence but will be capable of hybridizing to guinea pig PAR-4 DNA even in the presence of DNA oligonucleotides with mismatches. The mismatched DNA oligonucleotides may still sufficiently hybridize to the guinea pig PAR-4 DNA to permit identification and isolation of guinea pig PAR-4 encoding DNA. DNA isolated by these methods can be used to screen DNA libraries from a variety of cell types, from invertebrate and vertebrate sources, and to isolate homologous genes.

Purified biologically active guinea pig PAR-4 may have several different physical forms. Guinea pig PAR-4 may exist as a full-length nascent or unprocessed polypeptide, or as partially processed polypeptide or combinations of processed polypeptides. The full-length nascent guinea pig PAR-4 polypeptide may be postranslationally modified by specific proteolytic cleavage events that results in the formation of fragments of the full length nascent polypeptide. A fragment, or physical association of fragments may have the full biological activity associated with guinea pig PAR-4; however, the degree of guinea pig PAR-4 activity may vary between individual guinea pig PAR-4 fragments and physically associated guinea pig PAR-4 polypeptide fragments.

The amino acid sequence (SEQ.ID.NO.:3) encoded by the guinea pig PAR-4 cDNA including the guinea pig PAR-4 AP is provided below:

```
MWEPLLWLLVLGLGLAGSTSTPSVYDEDDVGLTGPWASSEAART

PQQVAPRSFPGQASANDSDVLELPDRLQVLLLGWAPTRLVPALYA

LALAVGLPANALALWVLARHGPRLPATALLMNLAAADLLLGLAL

PPRLVYHLRGQRWPLGEAACRVSTATLYGHMYGAALLLAAISLD

RYLALVHPLRARALRGRRLATGLCMSAWLGAATLAAPLALGRQT

FRLAGSGHLLCHDVLPLATQTAFWRPAFLCLAALGCFLPLLLMAL

CHGVTLCVLAAGSRRHSHALRLTALVLASAVAFFVPSNVLLLLHY

TDPSPGAGGELYGAYLPSLALSTLNSCVDPFLYYYASPEFRDKVRA

QLRCWLPRTTATSQGSQDVGSAGTGTHSLHP
```

This protein has a predicted molecular weight of about 41 kilodaltons, however, glycosylation and posttranslational modifications can increase the apparent molecular weight on an SDS-PAGE gel up to about 55 kD. Desired peptides can be obtained from this sequence and preferred peptides are at least 15 consecutive amino acids in length.

DNA encoding guinea pig PAR-4 cloned from a particular organism may be used to isolate and purify homologues of guinea pig PAR-4. To accomplish this, the first guinea pig PAR-4 DNA may be mixed with a sample containing DNA encoding homologues of guinea pig PAR-4 under appropriate hybridization conditions. The hybridized DNA complex may be isolated and the DNA encoding the homologous DNA may be purified therefrom.

Functional Derivatives/Variants

It is known that there is a substantial amount of redundancy in the various codons that code for specific amino acids. Therefore, this invention is also directed to those DNA sequences that contain alternative codons that code for the eventual translation of the identical amino acid. For purposes of this specification, a sequence bearing one or more replaced codons will be defined as a degenerate variation. Also included within the scope of this invention are mutations either in the DNA sequence or the translated protein, which do not substantially alter the ultimate physical properties of the expressed protein. For example, substitution of aliphatic amino acids alanine, valine, leucine and isoleucine; interchange of the hydroxyl residues serine and threonine, exchange of the acidic residues aspartic acid and glutamic acid, substitution between the amide residues asparagine and glutamine, exchange of the basic residues lysine and arginine and replacements among the aromatic residues phenylalanine or tyrosine may not cause a change in functionality of the polypeptide. Such substitutions are well known and are described, for instance in *Molecular Biology of the Gene, 4th* Ed. Bengamin Cummings Pub. Co. by Watson et al.

It is known that DNA sequences coding for a peptide may be altered so as to code for a peptide having properties that are different than those of the naturally occurring peptide. Methods of altering the DNA sequences include, but are not limited to site directed mutagenesis, chimeric substitution, and gene fusions. Site-directed mutagenesis is used to change one or more DNA residue resulting in a silent mutation, a conservative mutation, or a nonconservative mutation. Chimeric genes can be prepared by swapping domains of similar or different genes with similar domains in the guinea pig PAR-4 gene.

Fusion genes may be prepared that add domains to the guinea pig PAR-4 gene and these fusions can include, for example, the addition of an affinity tag to facilitate identification and isolation of the gene. Fusion genes may also be prepared that replace regions of the guinea pig PAR-4 gene, for example, with other sequences that encode amino acids that improve solubility. One or more transmembrane domains on a protein can be replaced or removed and a targeting sequence added to redirect the normal transport of the protein. In a preferred embodiment the protein domain associated with amino acids 219 to 243 of SEQ ID NO:3 is preserved. Other domains or regions of the protein can be replaced or substituted as desired. New post-translational modification sequences can also be added to the guinea pig PAR-4 gene. Exemplary sequences are known in the literature.

Other preferred variants of the present invention include fusion proteins containing portions of guinea pig PAR4 and portions of another mammalian PAR, particularly fusion proteins where one domain of a protein is exchanged for a homologous domain from another PAR. Such fusion proteins are used in functional studies of the receptor. In one such example, but not by way of limitation, one or more transmembrane helices are exchanged to determine the effect of the exchange on peptide activation of the receptor. In another example, but not by way of limitation, a fusion protein is produced that contains the extracellular domain of the guinea pig PAR4 and the transmembrane and intracellular domain of the human PAR4. Chimeric PAR1 genes have been described in the art (Gerazton et al (1994) Nature 368, 648–651) and the preparation of novel chimeric guinea pig PAR4 genes can be prepared using these techniques as well as using other methods known in the art. All such changes of the polynucleotide or polypeptide sequences are anticipated as useful variants of the present invention so long as the variant PAR-4 maintains at least one of its native characteristics.

Identity or similarity, as known in the art, are relationships between two or more polypeptide sequences or two or more polynucleotide sequences and can be determined by comparing the sequences. In the art, identity also means the degree of sequence relatedness between polypeptide or polynucleotide sequences, as the case may be, as determined by the match between strings of such sequences. Both identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity and similarity between two polynucleotide or two polypeptide sequences, both terms are well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., (1988) SIAM J. Applied Math., 48, 1073). Methods commonly employed to determine identity or similarity between sequences include, but are not limited to, those disclosed by Carillo, H., and Lipman, D., supra. Preferred methods to determine identity are designed to give the largest match between the sequences tested. Methods to determine identity and similarity are codified in computer programs. Preferred computer program methods to determine identity and similarity between two sequences include, but are not limited to, GCG program package (Devereux, J., et al., (1984) Nucleic Acids Research 12(1), 387), BLASTP, BLASTN, and FASTA (Atschul, S. F. et al., (1990) J. Molec. Biol. 215, 403).

The term "polynucleotide(s)" as used herein refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide" also includes DNAs or RNAs, as described above, that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are "polynucleotides" as the term is used herein. It will be appreciated that a great variety of modifications have been made to DNA and RNA that serve many useful purposes known to those of skill in the art. The term "polynucleotide" as it is employed herein embraces such chemically, enzymatically or metabolically modified forms of polynucleotides, as well as the chemical forms of DNA and RNA characteristic of viruses and cells, including simple and complex cells, inter alia. "Polynucleotides" further embraces short polynucleotides often referred to as oligonucleotide(s).

The term "polypeptides", as used herein, refers to the basic chemical structure of polypeptides that is well known and has been described in textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present invention are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *Proteins—Structure and Molecular Properties,* 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in *Posttranslational Covalent Modification of Proteins*, B. C. Johnson, Ed., Academic Press, New York (1983); Seifter et al., (1990) in *Meth. Enzymol.* 182, 626–646 and Rattan et al., "Protein Synthesis: Posttranslational Modifications and Aging", (1992) *Ann. N.Y. Acad. Sci.* 663, 48–62.

It will be appreciated, as is well known and as noted above, that polypeptides are not always entirely linear. For instance, non-linear polypeptides may be created as a result of posttranslational events such as natural processing events or events brought about by human manipulation. Circular, branched and branched circular polypeptides may be synthesized by non-translational natural processes or by entirely synthetic methods. Posttranslational modifications can occur anywhere in a polypeptide, including the peptide backbone, the amino acid side-chains and the amino or carboxyl termini. In fact, blockage of either an amino or carboxyl group in a polypeptide, or both, using for example, a covalent modification, occurs as part of the natural synthetic processing of polypeptides in situ and is used during the chemical synthesis of polypeptides as well. For example, the amino terminal residue of polypeptides made in *E. coli*, prior to proteolytic processing is almost invariably N-formylmethionine. During post-translational modification of the peptide, a methionine residue at the NH-terminus may then be deleted. Thus, this invention contemplates the use of both the methionine-containing and the methionineless amino terminal variants of the protein of the invention.

The modifications that occur in a polypeptide often will be a function of how it is made. For polypeptides made by expressing a cloned gene in a host, for instance, the nature and extent of the modifications are often determined by the host cell posttranslational modification capacity and the modification signals present in the polypeptide amino acid sequence. As is well known, glycosylation often does not occur in bacterial hosts such as, for example, *E. coli*. Therefore, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed inter alia to efficiently express mammalian proteins having native patterns of glycosylation.

Other modifications may be incorporated into the polypeptides of this invention and it will be appreciated that the same type of modification may be present in the same or varying degree at several sites in a given polypeptide. In general, as used herein, the term polypeptide encompasses all such modifications, particularly those that are present in polypeptides synthesized recombinantly by expressing a polynucleotide in a host cell.

Variant(s) of polynucleotides or polypeptides, as the term is used herein, are polynucleotides or polypeptides that differ from a reference polynucleotide or polypeptide, respectively. A variant of the polynucleotide may be a naturally occurring variant such as a naturally occurring allelic variant, or it may be a variant that is not known to occur naturally. The term "variant" is further used herein to describe: (1) A polynucleotide that differs in nucleotide sequence from another, reference polynucleotide and (2) A polypeptide that differs in amino acid sequence from another, reference polypeptide. Generally, nucleotide differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type a polynucleotide variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed above.

Generally, differences in the amino acid sequence of a polypeptide are limited so that the sequences of the reference and the variant are closely similar overall and, in many regions, identical. A variant and reference polypeptide may differ in amino acid sequence by one or more substitutions, additions, deletions, fusions and truncations, which may be present in any combination. As used herein, a "functional derivative" of guinea pig PAR-4 is a compound that possesses a biological activity (either functional or structural) that is substantially similar to the biological activity of guinea pig PAR-4. The term "functional derivatives" is intended to include the fragments, variants, degenerate variants, analogs and homologues as well as chemical derivatives of guinea pig PAR-4. Useful chemical derivatives of polypeptide are well known in the art and include, for example, covalent modifications of reactive organic sites contained within the polypeptide with a secondary chemical moiety. Well known cross-linking reagents are useful to react to amino, carboxyl, or aldehyde residues to introduce, for example, an affinity tag such as biotin, a fluorescent dye, or to conjugate the polypeptide to a solid phase surface (for example to create an affinity resin). The term "fragment" is meant to refer to any polypeptide subset of guinea pig PAR-4. A molecule is "substantially similar" to guinea pig PAR-4 if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire guinea pig PAR-4 molecule or to a fragment thereof. Further, particularly preferred in this regard are polynucleotides encoding variants, analogs, derivatives and fragments of SEQ.ID.NO.:2, and variants, analogs and derivatives of the fragments, which have the amino acid sequence of the polypeptide of SEQ.ID.NO.:3 in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the gene of SEQ.ID.NO.:2. Also especially preferred in this regard are conservative substitutions. Most highly preferred are polynucleotides encoding polypeptides having the amino acid sequence of SEQ.ID.NO.:3, without substitutions.

Further preferred embodiments of the invention are polynucleotides that are at least 75% identical over their entire length to a polynucleotide encoding the polypeptide having the amino acid sequence set out in SEQ.ID.NO.:3, and polynucleotides which are complementary to such polynucleotides. More preferably the polynucleotides encode protein with at least 75% identity to a polypeptide comprising amino acids 1 to 388 of SEQ ID NO:3. Alternatively, highly preferred are polynucleotides that comprise a region that is at least 80% identical, more highly preferred are polynucleotides at comprise a region that is at least 90% identical, and among these preferred polynucleotides, those with at least 95% are especially preferred. Furthermore, those with at least 97% identity are highly preferred among those with at least 95%, and among these those with at least 98% and at least 99% are particularly highly preferred, with at least 99% being the most preferred. The polynucleotides which hybridize to the above described polynucleotides in a preferred embodiment encode polypeptides which retain substantially the same biological function or activity as the polypeptide characterized by the deduced amino acid sequence of SEQ.ID.NO.:3. Preferred embodiments in this respect, moreover, are polynucleotides that encode polypeptides that retain substantially the same biological function or activity as the mature polypeptide encoded by the DNA of SEQ.ID.NO.:2.

The present invention further relates to polynucleotides that hybridize to the herein above-described sequences. In this regard, the present invention especially relates to polynucleotides that hybridize under stringent conditions to the herein above-described polynucleotides. As herein used, the term "stringent conditions" means hybridization will occur only if there is at least 95% and preferably at least 97% identity between the sequences. There are a large numbers of polynucleotide hybridization techniques known in the art including hybridizations coupling DNA to DNA, RNA to RNA and RNA to DNA. All of these methods can incorporate stringent hybridization conditions to facilitate the accurate identification of nucleic acid targeting to a hybridizable probe. As is known in the art, methods vary depending on the substrate used for hybridization and Maniatis et al. supra, as well as a variety of references in the art detail a number of stringent hybridization techniques. In one example, DNA or RNA samples to be probed are immobilized on a suitable substrate such as nitrocellulose, nylon, polyvinylidene difluoride, or the like. A purified probe, preferably with sufficient specific activity (generally greater than about $10^8$ cpm/μg probe), substantially free of contaminating DNA, protein or unincorporated nucleotides is used. Where nitrocellulose is used, and the immobilized nucleic acid is DNA immobilized on nitrocellulose, the nitrocellulose with DNA is incubated with a hybridization solution comprising 50% formamide-deionized, 6×SSC, 1% SDS, 0.1% Tween 20 and 100 μg/ml t RNA at 42° C. for 15 minutes. Probe is added and the nitrocellulose is further immobilized at 42° C. for about 12–19 hours. The nitrocellulose is then washed in at least two successive washes at 22° C. followed by stringent washes at 65° C. in a buffer of 0.04M sodium phosphate, pH 7.2, 1% SDS and 1 mM EDTA. Conditions for increasing the stringency of a variety of nucleotide hybridizations are well known in the art.

As discussed additionally herein regarding polynucleotide assays of the invention, for instance, polynucleotides of the invention may be used as a hybridization probe for RNA, cDNA and genomic DNA to isolate full-length cDNAs and genomic clones encoding the sequences of SEQ.ID.NO.:2 and to isolate cDNA and genomic clones of other genes that have a high sequence similarity to SEQ.ID.NO.:2. Such probes generally will comprise at least 15 bases. Preferably, such probes will have at least 30 bases and may have at least 50 bases. Particularly preferred probes will have at least 30 bases and will have 50 bases or less. For example, the coding region of the gene of the invention may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine to which members of the library the probe hybridizes.

The polypeptides of the present invention include the polypeptide of SEQ.ID.NO.:3 (in particular the mature polypeptide) as well as polypeptides which have at least 60% identity to the polypeptide of SEQ.ID.NO.:3, preferably at least 80% identity to the polypeptide of SEQ.ID.NO.:3, and more preferably at least 90% similarity (more preferably at least 90% identity) to the polypeptide of SEQ.ID.NO.:3 and still more preferably at least 95% similarity (still more preferably at least 97% identity) to the polypeptide of SEQ.ID.NO.:3. The invention further includes portions of such polypeptides with such portion of the polypeptide generally containing at least 30 amino acids and more preferably at least 50 amino acids. Representative examples of polypeptide fragments of the invention, include, for example, truncation polypeptides of SEQ.ID.NO.:3. Particular examples of truncations are those polypeptides encoding a functional domain of the guinea pig PAR-4 protein, such as the extracellular domain, or the transmembrane domain. Also preferred in this aspect of the invention are fragments characterized by structural or functional attributes of the polypeptide characterized by the sequences of SEQ.ID.NO.:3 such as alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, high antigenic index regions of the polypeptide of the invention, and combinations of such fragments. Preferred regions are those that mediate activities of the polypeptides of the invention. Most highly preferred in this regard are fragments that have a chemical, biological or other activity of the response regulator polypeptide of the invention, including those with a similar activity or an improved activity, or with a decreased undesirable activity.

Recombinant Expression of Guinea Pig PAR-4

The cloned guinea pig PAR-4 DNA obtained through the methods described herein may be recombinantly expressed by molecular cloning into an expression vector containing a suitable promoter and other appropriate transcription regulatory elements. The vector can be introduced into prokaryotic or eukaryotic host cells to produce recombinant guinea pig PAR-4 protein. Techniques for such manipulations are fully described in Maniatis, T. et al., supra, and are well known in the art.

Expression vectors are defined herein as heterologous DNA sequences that facilitate the transcription of a particular nucleic acid sequence and the translation of the resulting mRNA in an appropriate host. Such vectors can be used to express eukaryotic genes in a variety of hosts such as bacteria including *E. coli*. Other hosts include bluegreen algae, plant cells, insect cells, fungal cells including yeast cells, and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency. Expression vectors may include, but are not limited to, cloning vectors, modified cloning vectors, specifically designed plasmids or viruses.

A variety of mammalian expression vectors may be used to express recombinant guinea pig PAR-4 in mammalian cells. Commercially available mammalian expression vectors which may be suitable for recombinant guinea pig PAR-4 expression, include but are not limited to, pMAMneo (Clontech), pcDNA3 (Invitrogen), pMC1neo (Stratagene), pXT1 (Stratagene), pSG5 (Stratagene), pCINeo (Promega) EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and lZD35 (ATCC 37565) and other expression vectors that are known in the art.

A variety of bacterial expression vectors may be used to express recombinant guinea pig PAR-4 in bacterial cells. Commercially available bacterial expression vectors which may be suitable for recombinant guinea pig PAR-4 expression include, but not limited to pET vectors (Novagen) and pQE vectors (Qiagen).

A variety of fungal cell expression vectors may be used to express recombinant guinea pig PAR-4 in fungal cells such as yeast. Commercially available fungal cell expression vectors which may be suitable for recombinant guinea pig PAR-4 expression include but are not limited to pYES2 (Invitrogen) and *Pichia* expression vector (Invitrogen).

A variety of insect cell expression vectors may be used to express recombinant guinea pig PAR-4 in insect cells. Commercially available insect cell expression vectors which may be suitable for recombinant expression of guinea pig PAR-4 include, but are not limited to, pBlueBacII (Invitrogen) and pFastBac1 (Life Technologies).

DNA encoding guinea pig PAR-4 may be cloned into an expression vector for expression in a recombinant host cell. Recombinant host cells may be prokaryotic or eukaryotic including, but not limited to, bacteria such as *E. coli*, fungal cells such as yeast, mammalian cells including, but not limited to, cell lines of human, bovine, porcine, monkey and rodent origin, and insect cells including, but not limited to, *Drosophila* and silkworm derived cell lines. Cell lines derived from mammalian species which may be suitable and which are commercially available include, but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, and HEK-293 (ATCC CRL1573).

The expression vector may be introduced into host cells via any one of a number of techniques including, but not limited to, transformation, transfection, protoplast fusion, lipofection, and electroporation. The expression vector-containing cells are clonally propagated and individually analyzed to determine whether they produce guinea pig PAR-4 protein. Identification of guinea pig PAR-4 expressing host cell clones may be performed, for example, by assessing the immunological reactivity of a cell or of a protein with anti-guinea pig PAR-4 antibodies or by detecting the presence of host cell-associated functional guinea pig PAR-4 activity. Such activities include calcium mobilization in response to thrombin or exogenously added guinea pig PAR-4 AP.

Expression of guinea pig PAR-4 DNA may also be performed using in vitro produced synthetic mRNA. Synthetic mRNA or mRNA isolated from guinea pig PAR-4 producing cells can be efficiently translated in various cell-free systems, including, but not limited to, wheat germ extracts and reticulocyte extracts, as well as efficiently translated in cell based systems including, but not limited to, microinjection into frog oocytes.

To determine the guinea pig PAR-4 DNA sequence(s) that yields optimal levels of guinea pig PAR-4 activity and/or guinea pig PAR-4 protein, guinea pig PAR-4 DNA molecules including, but not limited to, the following can be constructed: the full-length open reading frame of the guinea pig PAR-4 cDNA encoding the [~41 kDa] protein (SEQ.ID.NO.:3) from approximately base [62] to approximately base [1225] (these numbers correspond to first nucleotide of first methionine and last nucleotide before the first stop codon of SEQ.ID.NO.:2) and several constructs containing portions of the cDNA encoding guinea pig PAR-4 protein. All constructs can be designed to contain none, all, or portions of the 5' or the 3' untranslated region of guinea pig PAR-4 cDNA.

Guinea pig PAR-4 activity and levels of protein expression can be determined following the introduction of these constructs into appropriate host cells. Preferably the guinea pig PAR-4 DNA cassette is optimized for protein expression in transient assays. Following optimization, the construct can be transferred to a variety of expression vectors, for expression in host cells including, but not limited to, mammalian cells, baculovirus-infected insect cells, *E. coli*, and the yeast *S. cerevisiae*.

Guinea Pig PAR-4 Activating Peptide

The guinea pig PAR-4 activating peptide SFPGQA-NH2 (SEQ ID No.:7) was synthesized and found to induce aggregation of guinea pig platelets with an $EC_{50}$ of 174±14.6 μM on guinea pig gel filtered platelets (n=6). Guinea pig PAR-4 AP also induced human platelet aggregation ($EC_{50}$ 140.5±2.5 μM on human gel filtered platelets (n=2)). These studies illustrated a notable flexibility in the evolution of the PAR-4 gene. Thus the present invention also provides a PAR-4 activating peptide (PAR-4 AP) comprising SFPGQ $(X)_n$(SEQ ID No. 11), where X is any amino acid or amino acid derivative, particularly fluorescent amino acid derivatives and where n is 0–30. Particularly preferred is the native guinea pig activating peptide, SFPGQA (SEQ.ID.NO.:7)

Clearly, the complexity of the thrombin receptor profile on platelets of different species will have a direct impact on the suitability of animal models to assess the role of PAR antagonists in thrombosis.

Assay Methods for Guinea Pig PAR-4

Host cell transfectants and microinjected oocytes may be used to assay both the levels of functional guinea pig PAR-4 activity and levels of total guinea pig PAR-4 protein by the following methods. In the case of recombinant host cells, this involves the co-transfection of one or possibly two or more plasmids, containing the guinea pig PAR-4 DNA encoding one or more co-receptors (Nakanishi-Matsui et al. (2000). *Nature* (*London*) 404:609–613) or subunits. In the case of oocytes, this involves the injection of synthetic RNAs for guinea pig PAR-4 protein. Following an appropriate period of time to allow for expression, cellular protein is metabolically labelled with, for example $^{35}$S-methionine for 24 hours, after which cell lysates and cell culture supernatants are harvested and subjected to immunprecipitation with polyclonal antibodies directed against the guinea pig PAR-4 protein.

Levels of guinea pig PAR-4 protein in host cells are quantitated by immunoaffinity and/or ligand affinity techniques. Cells expressing guinea pig PAR-4 can be assayed for the number of guinea pig PAR-4 molecules expressed by measuring the amount of a radioactive ligand, such as the guinea pig PAR-4 AP, binding to cell membranes. Guinea pig PAR-4-specific affinity beads or guinea pig PAR-4-specific antibodies are used to isolate for example $^{35}$S-methionine labeled or unlabeled guinea pig PAR-4 protein. Labeled guinea pig PAR-4 protein is analyzed by SDS-PAGE. Unlabeled guinea pig PAR-4 protein is detected by Western blotting, ELISA or RIA assays employing guinea pig PAR-4 specific antibodies.

Tissue and In Vivo Based Assays to Detect Guinea Pig PAR-4 Response

It is well known to those in the art that tissues are capable of responding to stimulation by agonists according to defined parameters. The term "agonist" here refers to a peptide, protein, or small molecule ligand of a receptor capable of activating cells within a particular tissue preparation. Since the PARs represent a particular class of GPCR activated by a protease, a protein with specific proteolytic activity such as trypsin or thrombin, can also serve as a ligand to selectively activate these PARs in a dose-dependent fashion. Moreover, the specific AP ligand of a particular PAR is able to elicit a selective and dose-dependent response from a tissue preparation (Al-Ani et al. (1995). *Can. J. Phys. Pharmacol.* 73:1203–1207; Hollenberg et al. (1996). *Mol. Pharmacol* 49:229–233; Roy et al. (1998). *Br. J. Pharmacol.* 123:1434–1440; Steinhoff et al. (2000). *Nat. Med.* (N.Y.) 6:151–158; Zheng et al. (1998). *J. Pharmacol. Exp. Ther.* 285:325–334). Likewise, these PAR APs can be used as probes to detect specific responses in vivo from intact animal studies (Cheung et al. (1998). *Can. J. Physiol. Pharmacol.* 76:16–25; Kawabata et al. (1998). *Br. J. Pharmacol.* 125:419–422; Kawabata et al. (2000). *Biochem. Biophys. Res. Commun.* 270:298–302; Kawabata et al. (2000). *Br. J. Pharmacol.* 129:1808–1814). Thus, the guinea pig PAR-4 AP is a useful tool to define selective PAR-4 responses in small animal models, since we have found that the guinea pig PAR-4 AP cross-activates human PAR-4 (FIG. 4). Therefore it is likely that it is capable of eliciting a selective PAR-4 response from a broad range of species.

The guinea pig PAR-4 protein can be detected in intact cells, membrane fractions of intact cells, as intact tissues, tissue samples or in organs or samples of organs. In one embodiment, detection of PAR-4 can be accomplished by detecting cell activation resulting from the association of the activating peptide with PAR-4. The cells and cell fractions can include any cell type expressing PAR-4 including recombinant cells and cell fractions, platelets and membrane fractions and tissues such as aortic ring samples, and the like. Activation of cells as a result of AP binding to PAR-4 can include platelet aggregation, calcium mobilization, ADP degranulation, cell shape change or other methods known in the art for detecting cell activation.

Similarly, these methods can be used to detect the ability of a particular test substance, such as an antibody, small molecule, peptide or the like to interfere with the association between AP and PAR-4. Such methods are well known in the art and can be readily adapted for the AP/PAR-4 molecules of this invention.

Production and Use of Antibodies that Bind to Guinea Pig PAR-4

Monospecific antibodies to guinea pig PAR-4 are purified from mammalian antisera containing antibodies reactive against guinea pig PAR-4 or are prepared as monoclonal antibodies reactive with guinea pig PAR-4 using techniques originally described by Kohler and Milstein, *Nature* 256: 495–497 (1975). Immunological techniques are well known in the art and described in, for example, *Antibodies: A laboratory manual* published by Cold Spring Harbor Laboratory Press, Cold Spring Harbor, N.Y., ISBN 0879693142. Monospecific antibody as used herein is defined as a single antibody species or multiple antibody species with homogenous binding characteristics for guinea pig PAR-4. Homogenous binding as used herein refers to the ability of the antibody species to bind to a specific antigen or epitope, such as those associated with the guinea pig PAR-4, as described above.

Guinea pig PAR-4 specific antibodies are raised by immunizing animals such as mice, rats, guinea pigs, rabbits, goats, horses and the like, with an appropriate concentration of guinea pig PAR-4 either with or without an immune adjuvant. In one embodiment of this invention polyclonal antisera is preferably raised in rabbits.

Preimmune serum is collected prior to the first immunization. Each animal receives between about 0.001 mg and about 1000 mg of guinea pig PAR-4 associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of guinea pig PAR-4 in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three-week intervals until maximal titers are obtained. At about 7 days after each booster immunization or about weekly after a single immunization, the animals are bled, the serum collected, and aliquots are stored at about –20° C.

Monoclonal antibodies (mAb) reactive with guinea pig PAR-4 are prepared by immunizing inbred mice, preferably Balb/c, with guinea pig PAR-4. The mice are immunized by the IP or SC route with about 0.001 mg to about 1.0 mg, preferably about 0.1 mg, of guinea pig PAR-4 in about 0.1 ml buffer or saline incorporated in an equal volume of an acceptable adjuvant, as discussed above. Freund's adjuvant is preferred, with Freund's complete adjuvant being used for the initial immunization and Freund's incomplete adjuvant used thereafter.

The mice receive an initial immunization on day 0 and are rested for about 2 to about 30 weeks. Immunized mice are given one or more booster immunizations of about 0.001 to about 1.0 mg of guinea pig PAR-4 in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag 4-1; MPC-11; S-194 and Sp2/0, with Sp2/0 being generally preferred.

The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using guinea pig PAR-4 as the antigen. The culture fluids are also tested, for example, in an Ouchterlony precipitation assay to determine the isotype of the mAb. Hybridoma cells from antibody positive wells are cloned by a technique such as the soft agar technique of MacPherson, *Soft Agar Techniques in Tissue Culture Methods and Applications*, Kruse and Paterson, Eds., Academic Press, 1973 or by the technique of limited dilution.

Monoclonal antibodies are produced in vivo by injection of pristane primed Balb/c mice, approximately 0.5 ml per mouse, with about $1 \times 10^6$ to about $6 \times 10^6$ hybridoma cells at least about 4 days after priming. Ascites fluid is collected at approximately 8–12 days after cell transfer and the monoclonal antibodies are purified by techniques known in the art.

In vitro production of anti-guinea pig PAR-4 mAb is carried out by growing the hybridoma in tissue culture media as is well known in the art. High density in vitro cell culture may be used to produce large quantities of anti-guinea pig PAR-4 mAbs using, for example, hollow fiber culture techniques, air lift reactors, roller bottle, or spinner flasks culture as is well known in the art. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of guinea pig PAR-4 in body fluids or tissue and cell extracts.

It is readily apparent to those skilled in the art that the above described methods for producing monospecific antibodies may be used to produce antibodies specific for guinea pig PAR-4 polypeptide fragments, or full-length nascent guinea pig PAR-4 polypeptide, or the individual guinea pig PAR-4 subunits. Specifically, it is readily apparent to those skilled in the art that monospecific antibodies may be generated which are specific for only one guinea pig PAR-4 subunit or the fully functional guinea pig PAR-4 protein. It is also apparent to those skilled in the art that monospecific antibodies may be generated that inhibit normal function of guinea pig PAR-4 protein.

Guinea pig PAR-4 antibody affinity columns are made by adding the antibodies to a gel support such that the antibodies form covalent linkages with the gel bead support. Preferred covalent linkages are made through amine, aldehyde, or sulfhydryl residues contained on the antibody. Methods to generate aldehydes or free sulfydryl groups on antibodies are well known in the art. As one example, amine groups are reactive with, for example, N-hydroxysuccinimide esters.

The invention can be better understood by way of the following examples. These examples are representative of the preferred embodiments, but are not to be construed as limiting the scope of the invention.

EXAMPLE 1

Isolation and Characterization of the Guinea Pig PAR-4 Gene

A probe corresponding to nucleotides 329 to 786 of human PAR-4 (Xu et al. (1998). *Proc. Natl. Acad. Sci. U.S.A.* 95:6642–6646; Genbank Accession AF055917) was $^{32}$P-labelled by random priming (Life Technologies) and used to screen $3 \times 10^6$ phage plaques of a λ FIX II guinea pig genomic library (Stratagene) under low stringency hybridization. Hybridizations were carried out using Rapid-hyb Buffer (AmershamPharmacia) for a minimum of 15 hr. at 55° C. Washes were carried out with two 20 min washes of 2× Standard Citrate Saline (SSC)/0.1% SDS, and two 20 min washes of 0.2×SSC/0.1% SDS at 55° C. Two positives were isolated and, following plaque purification, the entire genomic DNA inserts of both clones were independently subcloned into the Not I site of the plasmid vector pKS II (Stratagene). Restriction mapping indicated that these two genomic clones represented two distinct overlapping genomic fragments with sizes between 18 to 25-Kb. A cross-hybridizing 1.3-Kb Pst I restriction fragment, common to both genomic clones, was subcloned and subjected to sequence analysis. This fragment was found to contain all of the coding sequence in exon 2 from the presumptive activation sequence to the stop codon. Sequence surrounding this Pst I fragment was obtained by subjecting the original guinea pig PAR-4 genomic plasmid clones to partial sequence analysis and a compilation of this region is presented in SEQ.ID.NO.:1.

To identify sequences corresponding to exon 1, a second hybridization probe corresponding to nucleotides 104 to 249 (Genbank Accession AF055917) encoding the human PAR-4 NH$_2$-terminus was used to analyze Southern blots of the two original guinea pig PAR-4 genomic plasmid clones digested within the restriction enzyme Pst I. A common 300-bp cross-hybridizing Pst I fragment was identified, subcloned and subjected to sequence analysis. The sequence of this Pst I fragment was found to be identical to the original sequence obtained from the original genomic plasmid clones and indicated that this fragment resided adjacent to, and 5' of, the 1.3-Kb Pst I fragment encoding exon 2. Thus, unlike the first intron in the genes for PARs 1 and 2, which are on the order of ~10-Kb (Nystedt et al. (1995). *Eur. J. Biochem* 232:84–89; Nystedt et al. (1996). *J. Biol. Chem.* 270: 5950–5955; Li et al. (1996). *J. Biol. Chem.* 271:26320–26328; Kahn et al. (1996). *Mol. Med.* (Cambridge, Mass.) 2:349–357; Kahn et al. (1998). *J. Biol. Chem.* 273:23290–23296), intron 1 in the guinea pig PAR-4 gene was found to be much smaller ~150-bp.

Characterization of the Guinea Pig PAR-4 cDNA

To confirm the exact position and size of intron 1, PCR primers designed to span intron 1, GPP4 I1-U 5'-CAAC-CCCCAGTGTCTATGATGAGGATGA-3' (SEQ.ID.NO.:4) and GPP4 I1-L 5'-GCCCAGTGCAGCCAGACA-GAGAAAG-3' (SEQ.ID.NO.:5) were used to amplify the corresponding region from guinea pig platelet cDNA. Total RNA was isolated from guinea pig washed platelets using Trizol Reagent (Life Technologies, Grand Island, N.Y.). For conversion of RNA to first-strand cDNA, samples were incubated with random primers in the presence of Superscript II reverse transcriptase (Life Technologies) according to the manufacturer's recommendations. The PCR reaction was carried out on ca. 100 ng of guinea pig platelet cDNA using the Advantage-GC cDNA Polymerase Mix (Clontech) in a volume of 100 µl and at 30 cycles of 94° C. for 30 s/65.8° C. for 30 s/68° C. for 120 s. Following phenol/CHCl3 extraction and EtOH precipitation, the amplified product was incubated in 10 µl 1× Amplitaq buffer and 200 uM dNTP and Amplitaq (Perkin Elmer) at 72° C. 15 min to increase TA cloning efficiency. The amplified products were subcloned in pCR2.1 (Invitrogen) and six independent isolates subjected to sequence analysis to identify the exon/intron junction surrounding intron 1 and to deduce the complete amino acid sequence encoded by the mature guinea pig PAR-4 mRNA. The structure of the guinea pig gene is illustrated in FIG. 1 and the cDNA nucleotide sequence is provided in SEQ.ID.NO.:2 with the deduced amino acid sequence presented in SEQ.ID.NO.:3.

EXAMPLE 2

Platelet Aggregation

Human platelet-rich plasma (PRP) concentrate (Biological Specialties, Inc., Colmar, Pa.) was gel-filtered (Sepharose 2B, Pharmacia, Inc.) in Tyrode's buffer (140 mM NaCl, 2.7 mM KCl, 12 mM $NaHCO_3$, 0.76 mM $Na_2HPO_4$, 5.5 mM dextrose, 5.0 mM Hepes, and 2 mg/ml BSA, pH 7.4). Guinea pigs (400–800 g) were anesthetized and blood drawn via an intraarterial catheter. PRP was prepared by centrifugation at 200×g for 10 min. Guinea pig PRP was gel-filtered as above. Gel-filtered platelets were diluted with Tyrode's buffer (143,000 platelets/µl, per well) and 2 mM $CaCl_2$ in a 96-well microtiter plate. Platelet aggregation was initiated by the addition of the guinea pig PAR-4 AP (SFPGQA-NH2, SEQ ID No.:7) peptide. The assay plate was gently mixed constantly. Aggregation was monitored at 0 and 5 min after agonist addition in a microplate reader (Molecular Devices) by optical density at 650 nm (ΔSOFT). Aggregation was calculated as the decrease in optical density between the two measurements. All samples were tested in duplicate wells on the same plate.

Figure 3:
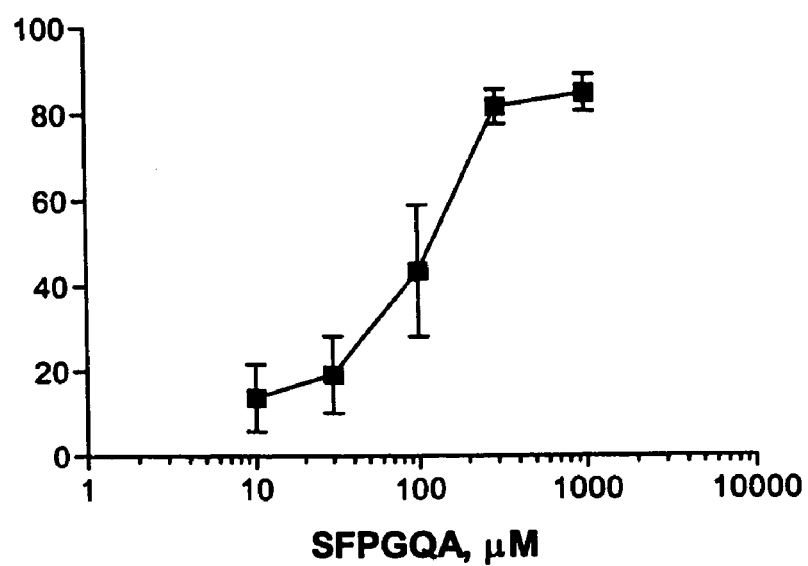
FIG. 3 is a graph illustrating the induction of human platelet aggregation by guinea pig PAR-4 AP.

As demonstrated in FIGS. 2 and 3, the synthetic guinea pig PAR-4 activating peptide induces the aggregation of guinea pig platelets with an $EC_{50}$ of 174±14.6 µM on guinea pig gel filtered platelets (n=6) and induces human platelet aggregation [$EC_{50}$ 140.5±2.5 µM on human gel filtered platelets (n=2)]. These studies illustrate a notable flexibility in the evolution of the PAR-4 gene. Clearly, the complexity of the thrombin receptor profile on platelets of different species will have a direct impact on the suitability of animal models to assess the role of PAR antagonists in thrombosis.

What is claimed is:

1. A substantially pure protein comprising a sequence of least 4 consecutive amino acids corresponding to amino acids 219 through 243 of SEQ ID NO:3.

2. The protein of claim 1 wherein the protein has a molecular weight of between 41–55 kD.

3. The protein according to claim 1, having the amino acid sequence as described in SEQ.ID.NO.:3.

4. A peptide consisting of 15 consecutive amino acids from SEQ ID NO:3.

* * * * *

SEQUENCE LISTING

```
<160> NUMBER OF SEQ ID NOS: 11

<210> SEQ ID NO 1
<211> LENGTH: 2428
<212> TYPE: DNA
<213> ORGANISM: Cavia porcellus

<400> SEQUENCE: 1
ggtgcccggg ttctggggcc ctggaaaggc tggagacagc acagtcactt tccggccatc      60
tctgtgtggg actggagcag gaaacgggcc acttgggagc cccaccctca gtttctgtta     120
ctgtcagggg cccggcctgg ccactgcctg gaaaatccct gtggtcaccc tgggaccact     180
ccacggacca ctctgctctg ctggcctgtg gaggacacca tagagacagc gggaacaggc     240
cacctgccca ctcacacact cgcagcctcc ctggtggcct tgggagtacc aggtcaccac     300
atcccacttt atctctgcag ctccggaagc tgccctgggt gacaaggcag gaagcgttgg     360
ccactgacga agggacggca gcatgtggga gcccctgctg tggctgctgg tgctggggct     420
cggcctggca ggtagcacct caaccccag tgtctatgat gaggatgacg gtgagtggcc     480
tggccttgag gtggggactc tgcccggggg agtagaatgt gggggccctg gccccagtgc     540
tggcttctcc cttccgagtc actgcctgtc tggtgctagt cccaagctgg gtccctgagc     600
cctctctccc ctctctgcag tgggcttgac agggccttgg gccagttctg aggcagcaag     660
gaccccacag caggtggccc cacgcagctt cccgggccag gcctctgcca acgacagtga     720
tgtgctggag ctgccggacc gcttgcaggt gctgctactg ggctgggcac ccacacggct     780
```

| | |
|---|---|
| ggtgcccgcg ctatatgcgc tggcactggc cgtggggctg ccggccaatg cactggcact | 840 |
| ctgggtcctg gcccgacatg gtccacggct gccggccacc gcgctgctca tgaatctggc | 900 |
| agccgccgac ctactgctgg gcctggcact gccccacgc cttgtctacc acctgcgtgg | 960 |
| ccagcgatgg cccctcgggg aagcggcctg ccgagtatcc acagccaccc tctacggtca | 1020 |
| catgtatggt gcagcgctgt tgctggctgc catcagcctg accgctacc tggcgctggt | 1080 |
| gcaccccctg cgtgcccgtg cgttgcgggg ccgccgcctg ccactgggc tctgcatgag | 1140 |
| tgcctggcta ggggccgcca cactggccgc acccctggcc ctggggcgcc agaccttccg | 1200 |
| cctggcaggc tccggccacc tgctctgtca tgatgtgctg ccactggcca cacagacagc | 1260 |
| cttctgcgg ccagccttc tctgtctggc tgcactgggc tgcttcctgc cgctgctgct | 1320 |
| catggcactg tgccatgggg tcacactgtg tgtgctggca gctggtagcc ggcgccacag | 1380 |
| ccatgcactg cgactcacgg cattggtgct ggcttctgct gtggccttct ttgtgcccag | 1440 |
| caatgtgctg ctgctgttgc actacacaga ccccagcccg ggtgccggtg gggaactgta | 1500 |
| cggtgcctac ctgcccagcc tggcgctcag caccctcaac agctgtgttg acccttcct | 1560 |
| gtactactac gcatcccctg agttccggga caaggtgcgg gcacagctgc gctgctggtt | 1620 |
| gcccaggacc actgccacat cccagggttc caagacgtg ggcagtgcag gcaccggtac | 1680 |
| tcactccttg cacccctgat ggctctgcga ccttggaggt tggaggcctc tgtcctgaag | 1740 |
| agggtacaca gtggccctgg cccaacgcag ctggaagtgc tctccaccca gaagtccctg | 1800 |
| ccactgtgga ccccatgggt cacggtcaca gcagccctgg gaacccaagg gctcaggtgc | 1860 |
| aggtccccac gatgtggccc cactgcagcc cagcctgtgc agccctgcct ccctggaagc | 1920 |
| cggcctgctt tcctctccac cccgccctgc ccccacacc caccacctgg tccctgtccc | 1980 |
| atctgcctgg cctcataggg tggggtggg gacacttgag ttgggctcac tgtggtccat | 2040 |
| gatgcttcca ataaaacctt aaaggacatg agacagcaaa atgtctggcc ctgcacaaac | 2100 |
| agggacagta caccctggca ctaaggtggg tctggggagg gcaggagcct cagtgatggg | 2160 |
| agggccctgt ggggagaggg gcagaggcag gccaagggat ggccaggtg ctggatgggt | 2220 |
| cgccaggcag ctgggtacag cagtccaagg gtacaggaaa gtggcctgca gcatttgaca | 2280 |
| gcactagggg aggccactct ggggcctgac ccagggctcc tgtgccagcc gagcttctgc | 2340 |
| ccaccaggct gcaccaggcc ccactatgct gatataggg cttgctaact tgcccaggct | 2400 |
| ggtcctgaac ttgctacctt cttcatct | 2428 |

<210> SEQ ID NO 2
<211> LENGTH: 1228
<212> TYPE: DNA
<213> ORGANISM: Cavia porcellus

<400> SEQUENCE: 2

| | |
|---|---|
| tccggaagct gccctgggtg acaaggcagg aagcgttggc cactgacgaa gggacggcag | 60 |
| catgtgggag cccctgctgt ggctgctggt gctggggctc ggcctggcag gtagcacctc | 120 |
| aaccccccagt gtctatgatg aggatgacgt gggcttgaca gggccttggg ccagttctga | 180 |
| ggcagcaagg accccacagc aggtggcccc acgcagcttc ccgggccagg cctctgccaa | 240 |
| cgacagtgat gtgctggagc tgccggaccg cttgcaggtg ctgctactgg ctgggcacc | 300 |
| cacacgctg gtgccgcgc tatatgcgct ggcactggcc gtggggctgc ggccactgc | 360 |
| actggcactc tgggtcctgg cccgacatgg tccacggctg ccggccaccg cgctgctcat | 420 |

-continued

```
gaatctggca gccgccgacc tactgctggg cctggcactg cccccacgcc ttgtctacca    480
cctgcgtggc cagcgatggc ccctcgggga agcggcctgc cgagtatcca cagccaccct    540
ctacggtcac atgtatggtg cagcgctgtt gctggctgcc atcagcctgg accgctacct    600
ggcgctggtg caccccctgc gtgcccgtgc gttgcggggc cgccgcctgg ccactgggct    660
ctgcatgagt gcctggctag gggccgccac actggccgca ccctggccc tggggcgcca     720 gaccttccgc ctggcaggct ccggccacct gctctgtcat gatgtgctgc cactggccac    780
acagacagcc ttctggcggc cagccttcct ctgtctggct gcactgggct gcttcctgcc    840
gctgctgctc atggcactgt gccatggggt cacactgtgt gtgctggcag ctggtagccg    900
gcgccacagc catgcactgc gactcacggc attggtgctg gcttctgctg tggccttctt    960
tgtgcccagc aatgtgctgc tgctgttgca ctacacagac cccagcccgg gtgccggtgg   1020
ggaactgtac ggtgcctacc tgcccagcct ggcgctcagc accctcaaca gctgtgttga   1080
ccccttcctg tactactacg catcccctga gttccgggac aaggtgcggg cacagctgcg   1140
ctgctggttg cccaggacca ctgccacatc ccagggttcc caagacgtgg gcagtgcagg   1200
caccggtact cactccttgc acccctga                                       1228
```

<210> SEQ ID NO 3
<211> LENGTH: 388
<212> TYPE: PRT
<213> ORGANISM: Cavia porcellus

<400> SEQUENCE: 3

```
Met Trp Glu Pro Leu Leu Trp Leu Leu Val Leu Gly Leu Gly Leu Ala
 1               5                  10                  15

Gly Ser Thr Ser Thr Pro Ser Val Tyr Asp Glu Asp Val Gly Leu
            20                  25                  30

Thr Gly Pro Trp Ala Ser Ser Glu Ala Ala Arg Thr Pro Gln Gln Val
        35                  40                  45

Ala Pro Arg Ser Phe Pro Gly Gln Ala Ser Ala Asn Asp Ser Asp Val
    50                  55                  60

Leu Glu Leu Pro Asp Arg Leu Gln Val Leu Leu Gly Trp Ala Pro
65                  70                  75                  80

Thr Arg Leu Val Pro Ala Leu Tyr Ala Leu Ala Leu Ala Val Gly Leu
                85                  90                  95

Pro Ala Asn Ala Leu Ala Leu Trp Val Leu Ala Arg His Gly Pro Arg
            100                 105                 110

Leu Pro Ala Thr Ala Leu Leu Met Asn Leu Ala Ala Ala Asp Leu Leu
        115                 120                 125

Leu Gly Leu Ala Leu Pro Pro Arg Leu Val Tyr His Leu Arg Gly Gln
    130                 135                 140

Arg Trp Pro Leu Gly Glu Ala Ala Cys Arg Val Ser Thr Ala Thr Leu
145                 150                 155                 160

Tyr Gly His Met Tyr Gly Ala Ala Leu Leu Leu Ala Ala Ile Ser Leu
                165                 170                 175

Asp Arg Tyr Leu Ala Leu Val His Pro Leu Arg Ala Arg Ala Leu Arg
            180                 185                 190

Gly Arg Arg Leu Ala Thr Gly Leu Cys Met Ser Ala Trp Leu Gly Ala
        195                 200                 205

Ala Thr Leu Ala Ala Pro Leu Ala Leu Gly Arg Gln Thr Phe Arg Leu
    210                 215                 220

Ala Gly Ser Gly His Leu Leu Cys His Asp Val Leu Pro Leu Ala Thr
```

-continued

```
                225                 230                 235                 240
    Gln Thr Ala Pro Trp Arg Pro Ala Phe Leu Cys Leu Ala Ala Leu Gly
                    245                 250                 255
    Cys Phe Leu Pro Leu Leu Met Ala Leu Cys His Gly Val Thr Leu
                260                 265                 270
    Cys Val Leu Ala Ala Gly Ser Arg Arg His Ser His Ala Leu Arg Leu
                275                 280                 285
    Thr Ala Leu Val Leu Ala Ser Ala Val Ala Phe Phe Val Pro Ser Asn
            290                 295                 300
    Val Leu Leu Leu His Tyr Thr Asp Pro Ser Pro Gly Ala Gly Gly
    305                 310                 315                 320
    Glu Leu Tyr Gly Ala Tyr Leu Pro Ser Leu Ala Leu Ser Thr Leu Asn
                    325                 330                 335
    Ser Cys Val Asp Pro Phe Leu Tyr Tyr Tyr Ala Ser Pro Glu Phe Arg
                340                 345                 350
    Asp Lys Val Arg Ala Gln Leu Arg Cys Trp Leu Pro Arg Thr Thr Ala
                355                 360                 365
    Thr Ser Gln Gly Ser Gln Asp Val Gly Ser Ala Gly Thr Gly Thr His
            370                 375                 380
    Ser Leu His Pro
    385

<210> SEQ ID NO 4
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 4 caaccccag tgtctatgat gaggatga                                           28

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 5
gcccagtgca gccagacaga gaaag                                             25

<210> SEQ ID NO 6
<211> LENGTH: 5
<212> TYPE: PRT
<213> ORGANISM: Artificial Sequence
<220> FEATURE:
<223> OTHER INFORMATION: Minimal Activating Peptide Sequence

<400> SEQUENCE: 6

Ser Phe Pro Gly Gln
1               5

<210> SEQ ID NO 7
<211> LENGTH: 6
<212> TYPE: PRT
<213> ORGANISM: Artificial Sequence
<220> FEATURE:
<223> OTHER INFORMATION: Guinea Pig PAR4 Activating Peptide

<400> SEQUENCE: 7
```

```
Ser Phe Pro Gly Gln Ala
1               5

<210> SEQ ID NO 8
<211> LENGTH: 6
<212> TYPE: PRT
<213> ORGANISM: Artificial Sequence
<220> FEATURE:
<223> OTHER INFORMATION: Human PAR1 Activating Peptide

<400> SEQUENCE: 8

Ser Phe Leu Leu Arg Asn
1               5

<210> SEQ ID NO 9
<211> LENGTH: 6
<212> TYPE: PRT
<213> ORGANISM: Artificial Sequence
<220> FEATURE:
<223> OTHER INFORMATION: Human PAR4 Activating Peptide

<400> SEQUENCE: 9

Gly Tyr Pro Gly Gln Val
1               5

<210> SEQ ID NO 10
<211> LENGTH: 6
<212> TYPE: PRT
<213> ORGANISM: Artificial Sequence
<220> FEATURE:
<223> OTHER INFORMATION: Murine PAR4 Activating Peptide

<400> SEQUENCE: 10

Gly Tyr Pro Gly Lys Phe
1               5

<210> SEQ ID NO 11
<211> LENGTH: 36
<212> TYPE: PRT
<213> ORGANISM: Artificial Sequence
<220> FEATURE:
<223> OTHER INFORMATION: Guinea Pig PAR4 Generic Activating Peptide
<220> FEATURE:
<221> NAME/KEY: MISC_FEATURE
<222> LOCATION: (7)..(36)
<223> OTHER INFORMATION: Xaa = any amino acid

<400> SEQUENCE: 11

Ser Phe Pro Gly Lys Phe Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa
        35
```